United States Patent
Besson

(10) Patent No.: US 6,351,514 B1
(45) Date of Patent: Feb. 26, 2002

(54) SLICE-ADAPTIVE MULTISLICE HELICAL WEIGHTING FOR COMPUTED TOMOGRAPHY IMAGING

(75) Inventor: Guy M. Besson, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/599,763

(22) Filed: Jun. 22, 2000

(51) Int. Cl.[7] .................................................. H01B 6/03
(52) U.S. Cl. .......................................... 378/15; 378/901
(58) Field of Search ................... 378/4, 15, 94

(56) References Cited

U.S. PATENT DOCUMENTS 5,881,122 A * 3/1999 Crawford et al. .............. 378/4
6,272,220 B1 * 8/2001 Pan et al. ..................... 378/15

* cited by examiner

Primary Examiner—David V. Bruce
(74) Attorney, Agent, or Firm—Armstrong Teasdale LLP; Christian G. Cabou

(57) ABSTRACT

In one embodiment, the present invention is a method for reconstructing at least one image representative of an object. This embodiment includes steps of: helically scanning the object with a multislice computed tomographic imaging system to acquire data representative of a plurality of computed tomographic image slices of an object including measurement data representative of conjugate rays; performing a minimum width helical interpolation of the acquired data to determine conjugate ray weights; increasing interpolation width when a sum of the conjugate ray weights is less than a threshold value; and filtering and backprojecting data to produce at least one image representative of the object. The filtering and backprojecting step includes weighting interpolated measurement data representative of conjugate rays using the increased interpolation width.

28 Claims, 1 Drawing Sheet

SLICE-ADAPTIVE MULTISLICE HELICAL WEIGHTING FOR COMPUTED TOMOGRAPHY IMAGING

BACKGROUND OF THE INVENTION

This invention relates generally to methods and apparatus for computed tomographic imaging systems, and more particularly to methods and apparatus for slice-adaptive multislice helical weighting for image reconstruction.

In at least one known computed tomography (CT) imaging system configuration, an x-ray source projects a fan-shaped beam which is collimated to lie within an X–Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Known single slice helical weighting algorithms typically rely on the conjugate measurements available for each ray for a $2\pi$ data set. Some known algorithms utilize significantly more than one source rotation, but these algorithms lead to broadened slice sensitivity profiles (SSP). Accordingly, for a single slice system using $2\pi$ worth of data, there exists little flexibility: two measurements are used to interpolate/extrapolate data onto a plane of reconstruction (POR). This algorithm does not vary with the helical pitch. At higher pitches, the measurements simply lie, on average, further away from the POR. Thus, SSP degrades monotonically with pitch.

In some CT imaging systems, the detector array is segmented so that a plurality of quasi-parallel slices of projection data is acquired and processed to construct a plurality of images corresponding to several slices though a volume. Such CT imaging systems are referred to as "multislice" systems. Multislice systems provide availability of more data. Therefore, looking up the conjugate ray and weighting accordingly as in single slice systems either leads to undesirable SSP broadening (such as in a "High Speed" mode, defined below) or a breakdown when a larger number of slices is considered (as when changing from 4 to 8 slices in "High Quality" mode). Another phenomenon associated with an increasing number of slices in multislice systems is that of helical weight cycles across a given projection fan. These helical weight cycles have a detrimental effect on image quality.

Increased flexibility in the choice of row or rows that provide data closest to the POR is possible with increasing amounts of data such as that made available by multislice CT imaging systems. This flexibility may exist at both ends of a given ray (i.e., for both conjugate measurements for the same ray through the patient). Where such flexibility is provided, a range of pitches exists for which measurements are available at least at two source locations. Measurements acquired at different source positions are known as "conjugate measurements." Pitches for which conjugate measurements are available are known as "High Quality" (HQ) pitches. When an HQ pitch is used, a CT imaging system is said to operate in "HQ mode." For a range of pitches for which measurements are available at only one source position, the availability of multislice data allows interpolation/extrapolation from different rows at the same source position. These pitches are known as "High Speed" (HS) pitches. When an HS pitch is used, a CT imaging system is said to operate in "HS mode." Higher HS pitches are made possible by allowing data extrapolation.

For a given helical pitch in HQ mode, a set of Radon points (or equivalently, a set of lines through a patient slice of interest) exists for which the conjugate measurements are offset by exactly half of the detected aperture $\Delta z$. ("Detector aperture" refers to an aperture on isocenter associated with one "macro detector row," or one measurement). For example, in one known four-slice scanner, a 3:1 pitch is selected for HQ mode because for all rays through isocenter $\gamma=0$), the conjugate measurements are exactly offset by $\Delta z/2$, half the aperture. In such a situation, a minimal z interpolation width is often used. However, this ideal sampling situation occurs only at a limited number of Radon points. Further away from isocenter, the offset gradually departs from optimum. The greater the number of rows (and correspondingly, the higher the pitch), the more rapid the departure from optimum. Further, a set of Radon points exists where the conjugate measurements exactly "face" one another (i.e., the z-offset between the two is zero). Although this situation is optimal when the associated rays are exactly in a plane of reconstruction (as these rays in effect define measurements as good as would be acquired in axial (step-and-shoot) scanning), sampling is at its worst when both rays are offset from the POR by exactly $\Delta z/2$. In the latter case, the POR lies exactly between two detector rows for both conjugate source positions.

An interpolation width equal to $\Delta z$ (base of triangle) leads to artifacts in the reconstructed image. In situations in which two conjugate measurements are exactly at the same z location, the only interpolation/extrapolation possible from these two samples (and these two samples only) with such a narrow interpolation width is a zeroth-order extrapolation of the measurements to the POR Indeed, if the two measurements are separated by $\epsilon$ in z, attempts at linear interpolation/extrapolation might be unstable due to noise and other inconsistencies in the projection data. While zeroth-order extrapolation per se might be acceptable, it leads to sudden discontinuities in the data synthesized at the POR when both measurements become offset from the POR by $\Delta z/2$. In this case, and as the z-offset varies with source rotation, the rows that are used for interpolation are incremented by 1. The measurements suddenly jump from row i to row i+1 (or i−1), introducing discontinuities that are amplified by the reconstruction filter and lead to streaks across the reconstructed image. Artifacts become particularly objectionable when the projection data vary rapidly from one row to the next, as when the patient anatomy varies rapidly in z.

Using 2Δz or any row-to-row interpolation, polynomial, etc., as a basis for a linear interpolation function leads to image quality trade-offs. Row-to-row discontinuities are reduced, as is the likelihood of streaking in a reconstructed image, but at a cost of significant slice broadening and z-resolution loss.

In one known helical weighting for a fan-beam, all rays corresponding to one row at a 6 o'clock source position are exactly in the POR, and accordingly should be weighted uniformly to 1.0. However, due to the helical scanning, conjugate rays across a conjugate arc will have variable distance in z from a corresponding conjugate detector row and the POR, and accordingly would see varying weights between 0 and 1.0. Upon normalizing the weights so that the sum of the weights is equal to 1.0, a weight function is obtained having a variation as a function of the fan-angle γ across the Scan Field of View (SFOV). This variation can lead to artifacts in reconstructed images because the derivative of the weight is discontinuous and a high-pass reconstruction filter is applied along γ.

With minimum width linear interpolation, rays across a reconstruction plane exist such that for both conjugate source locations, both measurements lie exactly between two detector rows, leading to a vanishing total weight. In practice, minimum width interpolation leads to a zeroth-order extrapolation estimate from two conjugate rows. With a small displacement of the ray in the reconstruction plane, the two row indices from which the estimate is defined are changed by 1. Therefore, any abrupt change in the data from row-to-row will lead to a discontinuity in the estimate. This discontinuity, after filter and backprojection, in turn leads to a streak across the reconstructed image.

It would therefore be desirable to provide methods and apparatus that avoid such undesirable SSP broadening and/or breakdown. It would also be desirable to provide methods and apparatus that reduce the detrimental effect of helical weight cycles on image quality. In addition, it would also be desirable to provide methods and apparatus that provide row-to-row interpolation only when justified by an underlying sampling.

BRIEF SUMMARY OF THE INVENTION

There is therefore provided, in one embodiment of the present invention, a method for reconstructing at least one image representative of an object. This embodiment includes steps of: helically scanning the object with a multislice computed tomographic imaging system to acquire data representative of a plurality of computed tomographic image slices of an object including measurement data representative of conjugate rays; performing a minimum width helical interpolation of the acquired data to determine conjugate ray weights; increasing interpolation width when a sum of the conjugate ray weights is less than a threshold value; and filtering and backprojecting data to produce at least one image representative of the object. The filtering and backprojecting step includes weighting interpolated measurement data representative of conjugate rays using the increased interpolation width.

Application of an adaptive, helical weighting algorithm leverages resolution inherently available from the available data, while reducing the likelihood of artifacts (such as streaks) arising from data inconsistencies across conjugate locations across rows.

DETAILED DESCRIPTION OF THE INVENTION

Figure 1:
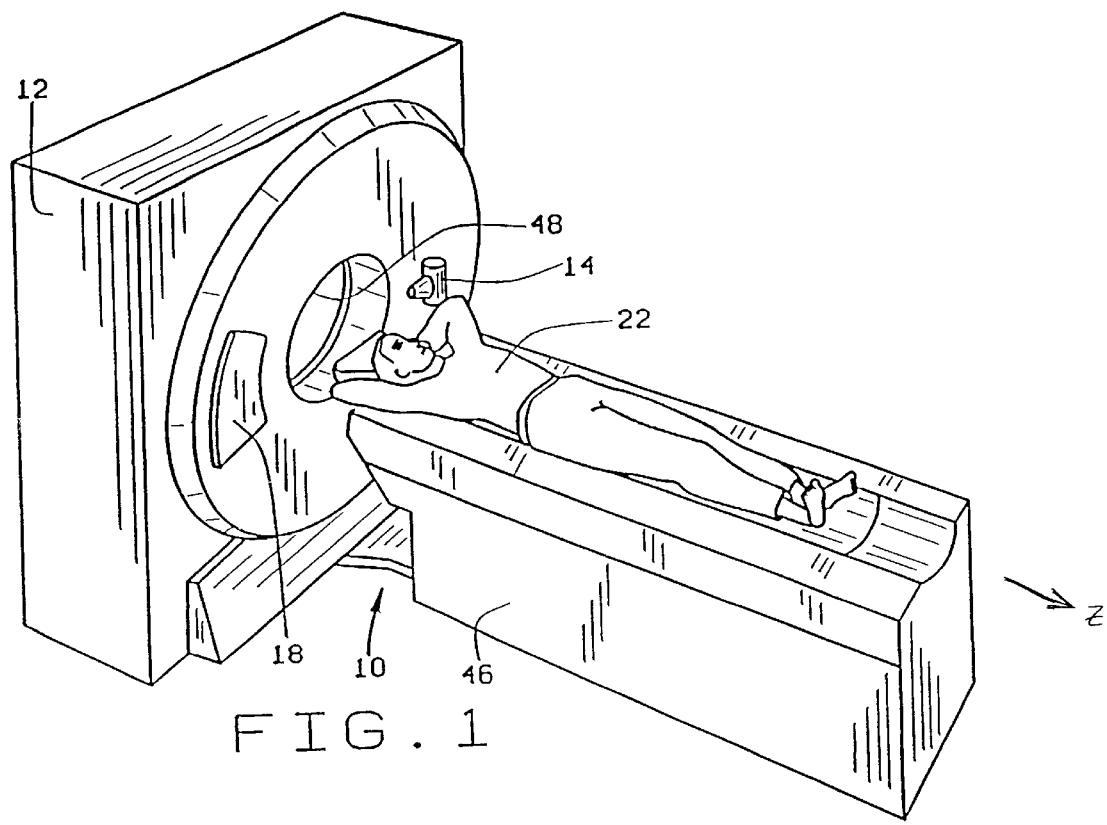
FIG. 1 is a pictorial view of a CT imaging system.
Figure 2:
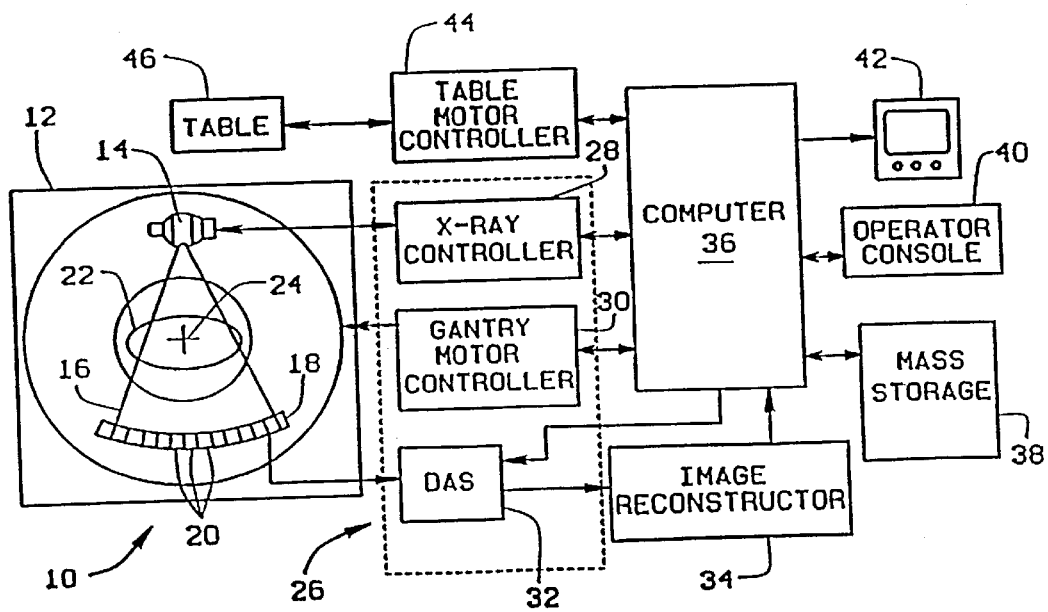
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

As described above, a minimum width linear interpolation results in weight cycles with linear segments and discontinuities of the first derivative, as well as points in Radon space where the total helical weights vanish (before normalization). These conditions lead to significant streak artifacts in the reconstructed images. Therefore, in one embodiment of the present invention, a changing interpolation width (and a change in points used to do a linear interpolation) is used adaptively to take into account different sampling conditions encountered across the reconstruction plane.

In one embodiment of the present invention, two loops are performed over the projections. In a first loop, starting with a minimum width helical interpolation, all conjugate ray weights (2 or 3 such measurements in an HQ mode of an 8-slice system at 7:1 pitch, for example) are calculated. When the sum of these weights is less than a selected threshold, the interpolation width is increased. Increasing the interpolation width, in effect, increases the contributions from all previously identified conjugate measurements, and leads to more measurements contributing to an estimate (or more conjugate measurements). For example, interpolation width is increased in one embodiment according to a condition written as:

$$\begin{cases} \text{if} \sum_{conjugate\ measurement} weights \leq T, \\ \text{then } hiw' = hiw \times f(T, \sum weights), \end{cases}$$

where f( )>1.0,

T is a preselected threshold, hiw is an initial helical interpolation width, and hiw' is the increased helical interpolation width.

One embodiment of the present invention includes certain measurements in an estimate depending on the distance of these measurements to the POR. Specifically, if the two measurements closest to the POR are on either side of the POR (and thus are necessarily conjugate measurements), then these two measurements are used to define a linear interpolation estimate. When the two measurements closest to the POR are on the same side of the POR, then the third closest measurement to the POR (which is then a conjugate measurement) is retained, and the first and third samples are used to define a linear interpolation estimate. In this case, the second and fourth closest measurements are then also conjugate measurements on either side of the POR, and in one embodiment are used to define a second estimate. Although this second estimate widens the slice profile, its use reduces patient x-ray dose, particularly when the direct and conjugate measurements happen to be closely located in z.

The above-described embodiments smooth the discontinuity of the weight first derivative. Although they change the definition of the weight, they do not necessarily completely eliminate the weight cycle across a given fan. In one embodiment, at least one or more additional step is used to reduce the discontinuity of the weight first derivative. Such additional steps include (1) applying a weight feathering function (as is used, for example, in a HE helical algorithm of one known scanning system); (2) applying a non-linear weighting functions; (3) rebinning acquired data to a parallel projection, and combining the weighted conjugate rays into a single measurement prior to filtering; and/or (4) using a fan-completion algorithm, whereby weighted conjugate measurements are combined with direct measurements to define a "completed" fan with uniform weight, to which reconstruction filtering is applied.

Where simultaneous access to direct and conjugate data is available, embodiments utilizing the fan-completion method completely eliminate the risks associated with filtering projections that have been modulated by helical weights with several cycles across the SFOV. Embodiments utilizing rebinning to either parallel or fan-parallel projections also completely eliminate this risk and significantly simplify the weighting algorithms.

From the preceding description of various embodiments of the present invention, it is evident that, for each ray through a patient (or Radon data point), at least two measurements at different source positions are provided. However, z-locations of these samples with respect to the POR vary across the image. Application of an adaptive, helical weighting algorithm leverages resolution inherently available from the available data, while reducing the likelihood of artifacts (such as streaks) arising from data inconsistencies across conjugate locations across rows. In some embodiments, weight cycle risk is also reduced. By calculating helical weights before actual scanning, based on known quantities, and passing a table of helical weights, computational load can be reduced. However, on-the-fly calculations enable more flexibility, such as that of scanning a volume with a pitch that varies during an acquisition.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

While the invention has been described in terms of various specific embodiments, those skilled in the art will recognize that the invention can be practiced with modification within the spirit and scope of the claims.

What is claimed is:

1. A method for reconstructing at least one image representative of an object comprising the steps of:

helically scanning an object with a multislice computed tomographic imaging system to acquire data representative of a plurality of computed tomographic image slices of the object including measurement data representative of conjugate rays;

determining conjugate ray weights;

increasing interpolation width when a sum of the conjugate ray weights is less than a threshold value; and filtering and backprojecting data to produce at least one image representative of the object, said filtering and backprojecting step including weighting interpolated measurement data representative of conjugate rays using the increased interpolation width.

2. A method in accordance with claim 1 wherein the conjugate ray weights are predetermined prior to said step of helically scanning the object.

3. A method in accordance with claim 1 wherein determining conjugate ray weights comprises performing a minimum width helical interpolation of the acquired data to determine the conjugate ray weights.

4. A method in accordance with claim 3 wherein increasing interpolation width when a sum of the conjugate ray weights is less than a threshold value comprises the step of increasing interpolation width according to a condition written as:

$$\begin{cases} \text{if} \sum_{conjugate\ measurement} weights \leq T, \\ \text{then } hiw' = hiw \times f(T, \sum weights), \end{cases}$$

where f( )>1.0,

T is a preselected threshold, hiw is an initial helical interpolation width, and hiw' is the increased helical interpolation width.

5. A method in accordance with claim 3 wherein performing a minimum width helical interpolation of the acquired data to determine conjugate ray weights comprises the step of utilizing two conjugate measurements closest to a plane of reconstruction to determine a linear interpolation estimate, the two conjugate measurements being on either side of the plane of reconstruction.

6. A method in accordance with claim 3 wherein performing a minimum width helical interpolation of the acquire data to determine conjugate ray weights comprises the step of utilizing two conjugate measurements to determine a linear interpolation estimate, wherein the two conjugate measurements are a closest measurement to a plane of reconstruction and a third closest measurement to the plane of reconstruction, and wherein a second closest measurement to the plane of reconstruction is on a same side of the plane of reconstruction as the closest measurement.

7. A method in accordance with claim 6, further comprising the step of determining a second linear interpolation estimate utilizing the second closest measurement and a fourth closest measurement to the plane of reconstruction.

8. A method in accordance with claim 3 wherein performing a minimum width helical interpolation of the acquired data to determine conjugate ray weights comprises the step of selectively including conjugate measurements in a linear interpolation estimate depending upon distances of the measurements from a plane of reconstruction.

9. A method in accordance with claim 8 wherein selectively including conjugate measurements in a linear interpolation estimate depending upon distances of the measurements from a plane of reconstruction comprises the step of utilizing two conjugate measurements closest to a plane of reconstruction to determine a linear interpolation estimate, when the two conjugate measurements closest to the place reconstruction are on either side of the plane of reconstruction, and utilizing a closest measurement to the plane of reconstruction and a third closest measurement to the plane of reconstruction, when a second closest measurement to the plane of reconstruction is on a same side of the plane of reconstruction as the closest measurement.

10. A method in accordance with claim 3 further comprising the step of applying a feathering function to the conjugate ray weights.

11. A method in accordance with claim 3 further comprising the step of applying a nonlinear weight function to the data.

12. A method in accordance with claim 3 further comprising the steps of rebinning the acquired data to a parallel projection, and combining the weighted conjugate rays into a single measurement prior to filtering.

13. A method in accordance with claim 3 further comprising the step of utilizing a fan-completion algorithm to combine weighted interpolated measurement data and acquired data to define a completed fan with uniform width prior to filtering and backprojecting the data.

14. A method in accordance with claim 3 wherein helically scanning an object with a multislice computed tomographic imaging system to acquire data representative of a plurality of computed tomographic image slices of the object including measurement data representative of conjugate rays comprises the step of scanning a volume of the object with a pitch that varies during the acquisition of the data.

15. A computed tomographic imaging system for reconstructing at least one image representative of an object, said system configured to:
helically scan an object to acquire data representative of a plurality of computed tomographic image slices of the object including measurement data representative of conjugate rays;
determine conjugate ray weights;
increase interpolation width when a sum of the conjugate ray weights is less than a threshold value; and
filter and backproject data including to produce at least one image representative of the object, the filtering and backprojecting of data including weighting of interpolated measurement data representative of conjugate rays using the increased interpolation width.

16. A system in accordance with claim 15 configured to predetermine the conjugate array weights prior to said system helically scanning the object.

17. A system in accordance with claim 15 wherein said system being configured to determine conjugate array weights comprises said system being configured to perform a minimum width helical interpolation of the acquired data to determine the conjugate ray weights.

18. A system in accordance with claim 17 wherein said system being configured to increase interpolation width when a sum of the conjugate ray weights is less than a threshold value comprises said system being configured to increase interpolation width according to a condition written as:

$$\begin{cases} \text{if} \sum_{conjugate\ measurement} weights \leq T, \\ \text{then } hiw' = hiw \times f(T, \sum weights), \end{cases}$$

where f( )>1.0,
T is a preselected threshold,
hiw is an initial helical interpolation width, and
hiw' is the increased helical interpolation width.

19. A system in accordance with claim 17 wherein said system being configured to perform a minimum width helical interpolation of the acquired data to determine conjugate ray weights comprises said system being configured to utilize two conjugate measurements closest to a plane of reconstruction to determine a linear interpolation estimate, the two conjugate measurements being on either side of the plane of reconstruction.

20. A system in accordance with claim 17 wherein said system being configured to perform a minimum width helical interpolation of the acquire data to determine conjugate ray weights comprises said system being configured to utilize two conjugate measurements to determine a linear interpolation estimate, wherein the two conjugate measurements are a closest measurement to a plane of reconstruction and a third closest measurement to the plane of reconstruction, and wherein a second closest measurement to the plane of reconstruction is on a same side of the plane of reconstruction as the closest measurement.

21. A system in accordance with claim 20, further configured to determine a second linear interpolation estimate utilizing the second closest measurement and a fourth closest measurement to the plane of reconstruction.

22. A system in accordance with claim 17 wherein said system being configured to perform a minimum width helical interpolation of the acquired data to determine conjugate ray weights comprises said system being configured to selectively include conjugate measurements in a linear interpolation estimate depending upon distances of the measurements from a plane of reconstruction.

23. A system in accordance with claim 22 wherein said system being configured to selectively include conjugate measurements in a linear interpolation estimate depending upon distances of the measurements from a plane of reconstruction. comprises said system being configured to utilize two conjugate measurements closest to a plane of reconstruction to determine a linear interpolation estimate, when the two conjugate measurements closest to the place reconstruction are on either side of the plane of reconstruction, and to utilize a closest measurement to the plane of reconstruction and a third closest measurement to the plane of reconstruction, when a second closest measurement to the plane of reconstruction is on a same side of the plane of reconstruction as the closest measurement.

24. A system in accordance with claim 17 further configured to apply a feathering function to the conjugate ray weights.

25. A system in accordance with claim 17 further configured to apply a nonlinear weight function to the data.

26. A system in accordance with claim 17 further configured to rebin the acquired data to a parallel projection, and to combine the weighted conjugate rays into a single measurement prior to filtering.

27. A system in accordance with claim 17 further configured to utilize a fan-completion algorithm to combine weighted interpolated measurement data and acquired data to define a completed fan with uniform width prior to filtering and backprojecting the data.

28. A system in accordance with claim 17 wherein said system being configured to helically scan an object to acquire data representative of a plurality of computed tomographic image slices of the object including measurement data representative of conjugate rays comprises the step of scanning a volume of the object with a pitch that varies during the acquisition of the data.

* * * * *

UNITED STATES PATENT AND TRADEMARK OFFICE
CERTIFICATE OF CORRECTION

PATENT NO.    : 6,351,514 B1
DATED         : February 26, 2002
INVENTOR(S)   : Besson It is certified that error appears in the above-identified patent and that said Letters Patent is hereby corrected as shown below:

Column 7,
Line 31, delete "place" and insert therefor -- plane of --.

Column 8,
Lines 9 and 12, delete "array" and insert therefor -- ray --.
Line 43, delete "acquire" and insert therefor -- acquired --.
Lines 66 & 67, delete "reconstruction. comprises" and insert therefor -- reconstruction comprises --.

Column 9,
Line 3, delete "place" and insert therefor -- plane of --.

Signed and Sealed this

Ninth Day of September, 2003

JAMES E. ROGAN
*Director of the United States Patent and Trademark Office*